United States Patent
Darcy et al.

(10) Patent No.: US 12,265,791 B2
(45) Date of Patent: *Apr. 1, 2025

(54) EMERGENCY WORKFLOW TRIGGER

(71) Applicant: WOEBOT LABS, INC., San Francisco, CA (US)

(72) Inventors: Alison Darcy, San Francisco, CA (US); Jade Daniels, San Francisco, CA (US); Casey Sackett, San Francisco, CA (US)

(73) Assignee: WOEBOT LABS, INC., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/597,409

(22) Filed: Mar. 6, 2024

(65) Prior Publication Data

US 2024/0370651 A1 Nov. 7, 2024

Related U.S. Application Data

(63) Continuation of application No. 17/364,001, filed on Jun. 30, 2021, now Pat. No. 11,954,437.

(Continued)

(51) Int. Cl.
*G06F 40/289* (2020.01)
*G06N 20/00* (2019.01)
(Continued)

(52) U.S. Cl.
CPC ......... *G06F 40/289* (2020.01); *G06N 20/00* (2019.01); *G16H 10/20* (2018.01); *G16H 20/70* (2018.01)

(58) Field of Classification Search
CPC .................................................. G06F 40/289
See application file for complete search history.

(56) References Cited

U.S. PATENT DOCUMENTS 5,961,332 A 10/1999 Joao
8,170,609 B2 5/2012 Hedtke et al.
(Continued)

FOREIGN PATENT DOCUMENTS

CN 102521220 A 6/2012
EP 4009192 A1 6/2022
(Continued)

OTHER PUBLICATIONS

Bickmore Timothy Wallace, "Relational Agents: Effecting Change through Human-Computer Relationships", Jan. 31, 2003, retrieved from internet Dec. 15, 2014; 284 pp.

(Continued)

*Primary Examiner* — Aryan E Weisenfeld
(74) *Attorney, Agent, or Firm* — NIXON PEABODY LLP

(57) ABSTRACT

Detection of crisis situations using multiple classifiers can enable fast and efficient processing of input phrases to determine if an abatement protocol should be executed. An input phrase can be passed through a pattern matching classifier and then through a trained machine learning classifier. If neither classifier identifies a crisis, the workflow can continue as usual. However, if a crisis is identified, confirmation of the crisis situation can be sought and used to further update one or both of the classifiers. If the crisis is confirmed, emergency information and crisis management tools can be presented to the user, among other mitigating actions. If the crisis is not confirmed, a prompt can be presented to the user to discuss the trigger phrase associated with the trigger signal.

24 Claims, 5 Drawing Sheets

Related U.S. Application Data

(60) Provisional application No. 63/120,810, filed on Dec. 3, 2020.

(51) Int. Cl.
*G16H 10/20* (2018.01)
*G16H 20/70* (2018.01)

(56) References Cited

U.S. PATENT DOCUMENTS

| | | | |
|---|---|---|---|
| 9,390,706 | B2 | 7/2016 | Gustafson et al. |
| 9,542,386 | B2 | 1/2017 | Andrade Silva et al. |
| 10,025,849 | B2 | 7/2018 | Kim et al. |
| 10,395,552 | B2 | 8/2019 | Clark et al. |
| 11,501,080 | B2 | 11/2022 | D'Souza et al. |
| 11,775,774 | B2 | 10/2023 | Darcy et al. |
| 11,797,825 | B2 | 10/2023 | Hashimoto et al. |
| 11,954,437 | B2 | 4/2024 | Darcy et al. |
| 11,972,212 | B2 | 4/2024 | Sackett et al. |
| 2005/0131739 | A1 | 6/2005 | Rabinowitz et al. |
| 2012/0173268 | A1 | 7/2012 | Omidi |
| 2016/0300570 | A1 | 10/2016 | Gustafson et al. |
| 2017/0193088 | A1 | 7/2017 | Boguraev et al. |
| 2017/0262755 | A1 | 9/2017 | Takeuchi et al. |
| 2017/0372029 | A1 | 12/2017 | Saliman et al. |
| 2019/0042563 | A1 | 2/2019 | Pestian et al. |
| 2019/0370412 | A1 | 12/2019 | Hammontree et al. |
| 2020/0019642 | A1 | 1/2020 | Dua et al. |
| 2020/0019863 | A1 | 1/2020 | Dua et al. |
| 2020/0020247 | A1 | 1/2020 | Simpson et al. |
| 2020/0118458 | A1 | 4/2020 | Shriberg et al. |
| 2020/0214626 | A1 | 7/2020 | Boyle |
| 2020/0227161 | A1 | 7/2020 | Hanson et al. |
| 2021/0074406 | A1 | 3/2021 | Eich et al. |
| 2021/0110895 | A1 | 4/2021 | Shriberg et al. |
| 2021/0182496 | A1 | 6/2021 | Shi et al. |
| 2021/0202065 | A1 | 7/2021 | Cummins et al. |
| 2021/0391083 | A1 | 12/2021 | Moturu et al. |
| 2022/0028541 | A1 | 1/2022 | Paull et al. |
| 2022/0115115 | A1 | 4/2022 | Paredes Castro |
| 2022/0269954 | A1 | 8/2022 | Harris et al. |
| 2022/0318311 | A1 | 10/2022 | Wang et al. |
| 2022/0327407 | A1 | 10/2022 | Trischler et al. |
| 2022/0335219 | A1 | 10/2022 | Sengupta et al. |
| 2023/0026871 | A1 | 1/2023 | Darcy et al. |
| 2023/0059946 | A1 | 2/2023 | Roy Chowdhury et al. |
| 2023/0215543 | A1 | 7/2023 | Darcy et al. |
| 2023/0215544 | A1 | 7/2023 | Darcy et al. |
| 2023/0394246 | A1 | 12/2023 | Darcy et al. |

FOREIGN PATENT DOCUMENTS

| | | |
|---|---|---|
| EP | 4123498 A1 | 1/2023 |
| EP | 4207207 A1 | 7/2023 |
| WO | WO 2019018280 A1 | 1/2019 |
| WO | WO 2021236616 A1 | 11/2021 |
| WO | WO2022174161 A1 | 8/2022 |

OTHER PUBLICATIONS

Crook Jordan, "911bot is a chat bot that could save your life", TechCrunch, May 8, 2016, 9 pp.

Darcy, et al., "Evidence of Human-Level Bonds Established With a Digital Conversational Agent: Cross-sectional, Retrospective Observational Study", JMIR Formative Research; vol. 5, No. 5, May 11, 2021, 7 pp.

jurafsky Daniel, et al., "Speech and Language Processing—An Introduction to Natural Language Processing, Computational Linguistics, and Speech Recognition—Third Edition Draft" In: Speech and Language Processing—An Introduction to Natural Language Processing, Computational Linguistics, and Speech Recognition—Third Edition draft Oct. 16, 2019, pp. 1-621; Oct. 16, 2019; XP055837804; 31 pp.

Pardeshi, et al., "A Survey on Different Algorithms used in Chatbot", International Research Journal of Engineering and Technology (IRJET), vol. 07, Issue 5, May 2020, 7 pp.

URSU, "Every Chatbot Needs and Exit", 7 pp. https://medium.com/the-chatbot-guru/chatbotexitsequence-7c45219e77a7, Nov. 22, 2019 (Year: 2019).

Woebot, Woebot Labs. (2018, Jan. 28). <https://woebot.io/> retrieved from Internet Archive Wayback Machine <https://web.archive.org/web/20180128215044/https://www.woebot.io/> on Sep. 29, 2023. (Year: 2018).

Yin Junjie, et al., "A Deep Learning Based Chatbot for Campus Psychological Therapy", arxiv.org, Cornell University Library; Oct. 9, 2019, 31 pp.

Yoshioka, et al., "BERT-based ensemble methods with data augmentation for legal textual entailment in COLIEE statute law task", Proceedings of the Eighteenth International Conference on Artificial Intelligence and Law, Jun. 2021; 278-284 pp.

Extended European Search Report for EP 21212394.7 dated Apr. 4, 2022.

Extended European Search Report for Application No. EP 22186577.7 dated Dec. 20, 2022; pp. 15.

Extended European Search Report for Application No. EP 22217098.7 dated Apr. 28, 2023; 10 pp.

EMERGENCY WORKFLOW TRIGGER

CROSS REFERENCE TO RELATED APPLICATIONS

The present application is a continuation of U.S. patent application Ser. No. 17/364,001, filed Jun. 30, 2021, which claims priority to and the benefit of U.S. Provisional Patent Application No. 63/120,810 filed Dec. 3, 2020, each of which is hereby incorporated by reference in its entirety.

TECHNICAL FIELD

The present disclosure relates to linguistic analysis generally and more specifically to providing emergency responses during natural language processing workflows.

BACKGROUND

Natural language processing (NLP) is used in many fields to provide a comfortable and relatable interface for various purposes. When a user communicates to a computer system via natural language, such as through text input (e.g., typing a message) or audio input (e.g., speaking a message), the computer system attempts to determine an intended meaning associated with the received input. For example, in the field of human psychology, artificial intelligence systems can use NLP to interact with the user and provide helpful tools, commentary, or other conversation with the user in a natural and comfortable fashion.

SUMMARY

The term embodiment and like terms are intended to refer broadly to all of the subject matter of this disclosure and the claims below. Statements containing these terms should be understood not to limit the subject matter described herein or to limit the meaning or scope of the claims below. Embodiments of the present disclosure covered herein are defined by the claims below, supplemented by this summary. This summary is a high-level overview of various aspects of the disclosure and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this disclosure, any or all drawings and each claim.

Embodiments of the present disclosure include a computer-implemented method, comprising: receiving an input phrase associated with a crisis situation; applying a first classifier on the input phrase to determine that the input phrase does not trigger the first classifier; applying a second classifier on the input phrase to determine that the input phrase triggers the second classifier, wherein the first classifier is one of a pattern matching classifier and a trained machine learning classifier, and wherein the second classifier is the other of the pattern matching classifier and the trained machine learning classifier; generating a trigger signal in response to determining that the input phrase triggers the second classifier; and executing an abatement protocol in response to generation of the trigger signal, wherein execution of the abatement protocol is intended to mitigate the crisis situation.

In some cases, executing the abatement protocol includes i) accessing and presenting a text string containing emergency contact information, ii) accessing and presenting a link configured to facilitate an emergency contact connection upon actuation; iii) sending a signal to automatically facilitate an emergency contact connection; iv) initiating a patient health questionnaire protocol; v) generating a prompt for selecting a crisis management tool; vi) automatically initiating a crisis management tool; or vii) any combination of i-vi. In some cases, the method further comprises presenting a crisis confirmation prompt in response to determining that the input phrase triggers the second classifier; and receiving a confirmation response in response to presenting the confirmation prompt, the confirmation response including a confirmation of the crisis situation or a denial of the crisis situation, wherein executing the abatement protocol occurs in response to receiving the confirmation of the crisis situation.

In some cases, the method further comprises identifying a trigger phrase in response to determining that the input phrase triggers the second classifier, wherein the trigger phrase includes a portion of the input phrase that matched a regular expression when the second classifier is the pattern matching classifier, and wherein the trigger phrase includes the input phrase when the second classifier is the trained machine learning classifier; and presenting a denial prompt in response to receiving the denial of the crisis situation, wherein presenting the denial prompt includes using the trigger phrase. In some cases, the method further comprises logging the confirmation response in association with the trigger phrase; and updating at least one of the first classifier and the second classifier using the logged confirmation response and the trigger phrase. In some cases, executing the abatement protocol includes scheduling a follow-up contact for a future time, wherein the method further comprises presenting a follow-up message at the future time, and wherein presenting the follow-up message includes presenting the trigger phrase.

In some cases, the method further comprises determining a crisis score using the input phrase, wherein generating the trigger signal is further based on a determination that the crisis score is outside of a threshold range. In some cases, the method further comprises determining a crisis score using the input phrase; accessing one or more historical crisis scores; determining a crisis score trend using the crisis score and the one or more historical crisis scores; and determining a future crisis score using the crisis score and the crisis score trend, wherein generating the trigger signal is further based on a determination that the future crisis score is outside of a threshold range. In some cases, the first classifier is the pattern matching classifier and the second classifier is the trained machine learning classifier. In some cases, the trained machine learning classifier is trained using a set of training input phrases that were determined to not trigger the pattern matching classifier. In some cases, the trained machine learning classifier is trained using a set of training input phrases including a first subset of training input phrases associated with crisis situations and a second subset of training input phrases not associated with crisis situations.

Embodiments of the present disclosure include a system comprising one or more data processors; and a non-transitory computer-readable storage medium containing instructions which, when executed on the one or more data processors, cause the one or more data processors to perform the above method.

Embodiments of the present disclosure include a computer-program product tangibly embodied in a non-transitory machine-readable storage medium, including instructions configured to cause a data processing apparatus to perform the above method.

BRIEF DESCRIPTION OF THE DRAWINGS

The specification makes reference to the following appended figures, in which use of like reference numerals in different figures is intended to illustrate like or analogous components.

DETAILED DESCRIPTION

Figure 1:
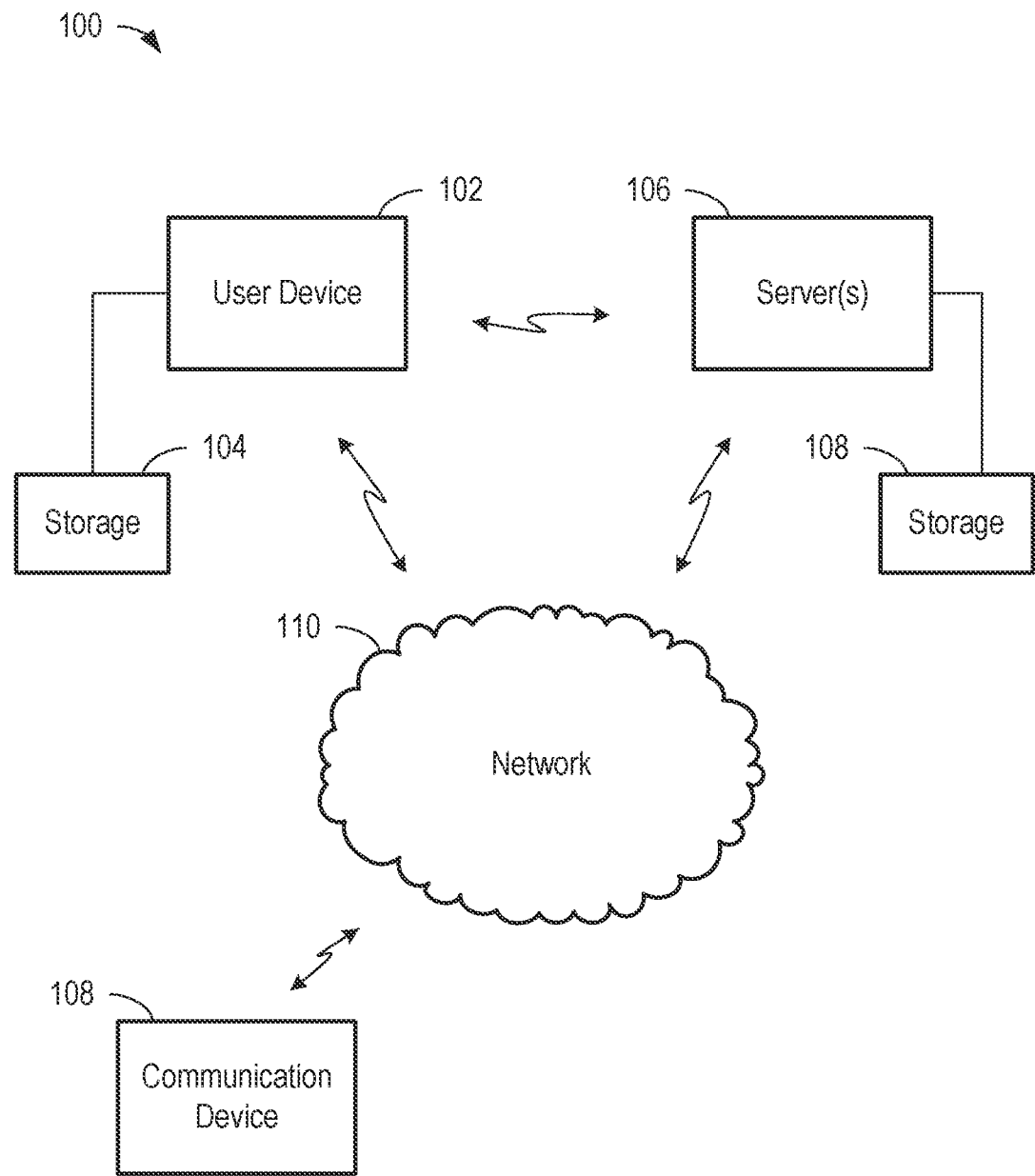
FIG. 1 is a schematic diagram depicting a computing environment according to certain aspects of the present disclosure.

Certain aspects and features of the present disclosure relate to a natural language processing (NLP) system capable of detecting crisis situations through the use of multiple classifiers. The use of multiple classifiers can enable fast and efficient processing of input phrases to determine if an abatement protocol should be executed. An input phrase can be passed through a pattern matching classifier and then through a trained machine learning classifier. If neither classifier identifies a crisis, the workflow can continue as usual. However, if a crisis is identified, confirmation of the crisis situation can be sought and used to further update one or both of the classifiers. If the crisis is confirmed, emergency information and crisis management tools can be presented to the user, among other mitigating actions. If the crisis is not confirmed, a prompt can be presented to the user to discuss the trigger phrase associated with the trigger signal.

Aspects and features of the present disclosure can be used in various environments and for various purposes. In some cases, aspects and features of the present disclosure enable automatic detection of crisis situations based on received input, which can be especially useful in human-computer interactions, such as artificial intelligence chat-based tools, commonly known as chatbots. In some cases, the present disclosure can be especially useful when used with chatbots used for therapy, such as the monitoring and/or treatment of mental health disorders. In such cases, it can be especially important to identify whether or not an individual interacting with the chatbot is undergoing a crisis situation. If a crisis situation is detected, the chatbot (optionally after confirmation from the individual) can execute a protocol that includes taking actions to help mitigate the crisis situation or otherwise aid the individual in managing the crisis situation. As used herein with respect to a crisis situation, the term "mitigate" is inclusive of both affecting the crisis situation itself, as well as affecting the individual to better manage or undergo the crisis situation. In cases where a chatbot is used, inputs are normally received in the form of text selected from a list or entered into a field, although that need not always be the case. For example, in some cases, individuals can speak or dictate to the chatbot.

While described with reference to a chatbot in many places herein, certain aspects and features of the present disclosure can be used for other purposes, such as to detect crisis situations in other human-computer interactions, such as personal journaling applications, voice-activated devices (e.g., voice-activated assistants), voice-activated telephonic prompts (e.g., a voice-activated menu service for a telephone line), and the like. Certain aspects and features of the present disclosure can also be used to detect crisis situations in human-human interactions, such as text-based or audio-based communications between individuals locally or remotely. For example, a therapist treating a patient may make use of a system that automatically detects the patient's interactions to identify whether or not a crisis situation may be occurring, notifying the therapist or making a log entry when a crisis situation is detected.

While many applications of the aspects and features of the present disclosure are especially useful for automatic and dynamic crisis detection, such as realtime crisis detection, that need not always be the case. In some cases, an input phrase can be stored for later processing, only being processed at a later time to identify whether or not a crisis situation occurred when the input phrase was supplied. In such cases, various actions, such as execution of an abatement protocol, can still be performed.

An individual can provide an input phrase, such as via text entry in a chat box, by selecting a text entry, by speaking words aloud, or otherwise. The term input phrase is inclusive of any suitable collection of inputs that conveys linguistic meaning, such as a single word, multiple words, a single sentence, multiple sentences, or even symbols (e.g., emoticons and the like). The input phrase can be pre-processed as necessary to achieve a standard type of input for the classifiers (e.g., an audio signal can be processed through a speech-to-text processor to generate corresponding text).

The input phrase can be processed by a pattern matching classifier and a trained machine learning classifier (optionally sequentially in that order) to determine if at least one classifier returns a trigger signal. If at least one of (or optionally both of) the classifiers returns a trigger signal, a trigger signal can be sent to initiate a crisis workflow, optionally including a trigger phrase (e.g., the input phrase or a portion of the input phrase that caused the classifier to trigger) and/or other information.

The crisis workflow can request confirmation from the individual that a crisis situation does exist. The confirmation can be stored, optionally along with the trigger signal and/or other information, and later used to improve future classification. If the crisis situation is confirmed, an abatement protocol can be executed, which can include i) accessing and presenting a text string containing emergency contact information, ii) accessing and presenting a link configured to facilitate an emergency contact connection upon actuation; iii) sending a signal to automatically facilitate an emergency contact connection; iv) initiating a patient health questionnaire protocol; v) generating a prompt for selecting a crisis management tool; vi) automatically initiating a crisis management tool; or vii) any combination of i-vi. In some cases, a follow-up can be automatically or manually scheduled, which can then be used to present a follow-up message some time in the future to check in on the individual.

In some cases, if the crisis situation is denied, a denial prompt can be present to obtain more information about why the detected crisis situation was denied, and/or provide information that may be useful to one who denied the crisis situation. In some cases, presenting a denial prompt can include using the trigger phrase, such as presenting the trigger phrase and asking the individual why the trigger phrase is not indicative of a crisis situation, asking why the individual provided the trigger phrase, and/or what the trigger phrase evoked in the individual.

The use of both a pattern matching classifier and a trained machine learning classifier has been found to be especially useful for classification of crisis situations. In the detection of crisis situations, it can be important to maximize different aspects of the performance of the classifier(s). For example, it can be detrimental to fail to classify too many input phrases that were actually crisis situations, as these individuals may not receive beneficial and important help. Additionally, it can be detrimental to falsely classify too many non-crisis input phrases as crisis situations, as it can annoy users and discourage individuals from making use of the underlying systems (e.g., the chatbot). Depending on the needs associated with the particular use case, it can be important to maximize or minimize different operational statistics of one or both classifiers. Additionally, while use of a trained machine learning classifier (e.g., a trained neural network classifier) is useful for detecting crisis situations that would not otherwise be captured by the pattern matching classifier, the use of the pattern matching classifier is useful to detect certain words, collections of words, or other patterns that may always be indicative of a crisis situation or that may be strongly indicative of a crisis situation.

A pattern matching classifier can be any suitable classifier that uses matching criteria to identify whether or not the input phrase fits the matching criteria. In some cases, simple pattern matching classifiers can include find or search functions that simply determine whether or not a certain word or collection of words is present in the input phrase. In some cases, more complex pattern matching classifiers can be used, such as a regular expression (RegEx) classifier. In such cases, the matching criteria can be the regular expressions used to determine whether or not the input phrase first matches the set of regular expressions. For example, a regular expression can be "\bkill\W\+(?:\w+\W+){1,6}? (\w+){0,}self" and can search for instances of words containing "self" within six words of the word "kill." A set of regular expressions can include one or more inclusionary regular expressions and/or one or more exclusionary regular expressions. In some cases, use of a RegEx classifier has been especially useful, although any suitable pattern matching classifier may be used. The pattern matching classifier can be a classifier that does not use a trained machine learning model.

A trained machine learning classifier is any suitable classifier that uses machine learning to train the classifier, such as using supervised or unsupervised training. The classifier can be a machine learning model. Any suitable machine learning model classifier can be used, such as a neural network classifier or deep neural network classifier. In some cases, a recurrent neural network (RNN), optionally with a long short-term memory (LSTM) architecture, can be used. In some cases, the machine learning model can be a transformer-based model, which can process a full input phrase at a time, rather than a RNN, which may process individual tokens of an input phrase one-at-a-time. In some cases, the trained machine learning classifier can be a model that is pretrained for use with language, and then further trained or fine-tuned specifically for detection of crisis situations. Examples of pretrained transformer-based models include a Generative Pretrained Transformer 2 (GPT-2) model and a Bidirectional Encoder Representations from Transformers (BERT) model. Training (e.g., initial training or further training) and/or fine-tuning can include using training data that includes a set of input phrases comprising a subset of input phrases associated with a crisis situation and a subset of input phrases not associated with a crisis situation. In some cases, use of a BERT classifier has been especially useful, although any suitable trained machine learning classifier may be used.

When classifiers are being compared, updated, trained, and otherwise improved, metrics about the performance of the classifier can be obtained. Such metrics are often based on the different possible outcomes to the classification of an input phrase. The outcome for each input phrase can be i) a true positive (TP), representing a correct classification as a crisis situation; ii) a false positive (FP), representing an incorrect classification as a crisis situation; iii) a false negative (FN), representing an incorrect determination that no crisis situation exists; and iv) a true negative (TN), representing a correct determination that no crisis situation exists. In some cases, the knowledge of whether or not a classification is correct can be based on existing training data. In some cases, however, knowledge of whether or not a classification is correct can be based on logged confirmation responses, as disclosed herein.

Using an example dataset of 17,030 input phrases, classifiers were prepared and used to determine whether or not a crisis situation was detected. This example dataset was processed through multiple NLP systems, each with a different classifier structure, the results of which are provided in the table below. In a first example, identified as "Pattern Match Only 1," the dataset was processed by only a RegEx classifier that included a set of inclusionary and exclusionary regular expressions. In a second example, identified as "Pattern Match Only 2," the dataset was processed by only a RegEx classifier that was similar to the classifier of Pattern Match Only 1, except without exclusionary regular expressions and with a more limited set of inclusionary regular expressions. In a third example, identified as "Pattern Match+Trained Machine Learning," the dataset was processed by a dual classifier including a RegEx classifier and a BERT classifier, such as described herein according to certain aspects and features of the present disclosure.

|  | Pattern Match Only 1 | | Pattern Match Only 2 | | Pattern Match + Trained Machine Learning | |
| --- | --- | --- | --- | --- | --- | --- |
| Confusion Matrix | 68 | 1702 | 56 | 1714 | 1724 | 46 |
|  | 70 | 15190 | 14 | 15246 | 78 | 15182 |
| Accuracy | 0.8959 | | 0.8959 | | 0.9927 | |
| Sensitivity | 0.0384 | | 0.0384 | | 0.9740 | |
| Specificity (Recall) | 0.9954 | | 0.9954 | | 0.9949 | |
| Precision | 0.0044 | | 0.0044 | | 0.1020 | |
| F-Score | 0.8541 | | 0.8541 | | 0.9927 | |

As seen in the table above, the initial Pattern Match Only 1 classifier was able to achieve a somewhat strong accuracy and specificity, but left room for improvement, especially with respect to the large number of instances of false positives and the overall low precision and sensitivity. Modifications were made to Pattern Match Only 1 to create the Pattern Match Only 2 classifier, and while the Pattern Match Only 2 classifier did significantly reduce the number of false negatives, it still maintained a large number of false positives and fewer true positives. In the Pattern Match+Trained Machine Learning classifier, the number of true positives increased dramatically and the number of false positives decreased dramatically, all with only a slight increase in the number of false negatives. Some trials (not depicted in the table above) included use of only a trained machine learning classifier, but it was determined that a combination of a Pattern Match classifier and a trained machine learning classifier would be more beneficial. Such a combination is especially more beneficial in production environments since the pattern matches may improve generalization and ensure a match against certain critical patterns.

Through various trials, it was determined that use of a pattern matching classifier (e.g., a RegEx classifier) and a trained machine learning classifier (e.g., a BERT classifier) was beneficial, as it could provide excellent performance. The pattern matching classifier could be adjusted to minimize the number of false positives and false negatives created, while still ensuring that certain key trigger phrases would be captured, all while the trained machine learning classifier can be used to pick up other crisis situations that would otherwise not be captured by the pattern matching classifier. Therefore, at least with reference to the figures below, in some cases, reference to a pattern matching classifier can be considered as reference to a RegEx classifier, and/or reference to a trained machine learning classifier can be considered as reference to a BERT classifier.

The pattern matching classifier and trained machine learning classifier can be used in any suitable order, including simultaneously. However, in some cases, it can be beneficial to have the input phrase be processed by the pattern matching classifier first, before being sent to the trained machine learning classifier. In such cases, the pattern matching classifier, which is often a faster operating classifier, can quickly determine whether or not the input phrase fits in its definition as a crisis situation. If so, the crisis workflow can be started immediately. However, if the pattern matching classifier does not classify the input phrase as a crisis situation, that input phrase can be passed to the trained machine learning classifier for classification. Thus, the trained machine learning classifier may only ever receive a subset of the full set of input phrases, namely those input phrases that the pattern matching classifier deems are not crisis situations. In some cases, the trained machine learning classifier can be trained (e.g., fine-tuned) based on a full set of training data. However, in some cases, the trained machine learning classifier can be trained only on input phrases that have already been classified by the pattern matching classifier as not crisis situations.

In some cases, prior to attempting to detect a crisis situation from an input phrase and/or upon detecting a crisis situation, the NLP system can present the user with a competence statement. The competence statement can be an indication of the limits of the NLP system's ability to detect crisis situations and the limits of actions that the NLP system may be able to take. In some cases, the competence statement can be updated automatically using the current operational statistics of the classifiers used to detect crisis situations. In some cases, the competence statement can be updated automatically based on the available actions the NLP system can perform in response to detection of the crisis situation. In an example, an NLP system with no ability to direct emergency personnel to the user's location may indicate such limitations in the competence statement. The competence statement can be tailored to provide adequate notice to a user based on generally accepted ethical principles of boundaries of competence, such as those promulgated by the American Psychological Association or the Psychological Society of Ireland.

Aspects and features of the present disclosure provide various improvements to the technological process of natural language processing, especially with respect to handling crisis situations. Examples of such improvements include substantial increases to accuracy and/or sensitivity without compromising specificity. Further, certain aspects and features of the present disclosure enable an administrator to maximize or minimize different operational statistics of one or more classifiers, allowing the administrator to customize the overall classifying performance of the system in a new way. Additionally, certain aspects of the present disclosure, including the use of a RegEx classifier combined with a trained machine learning classifier provide specific improvements to the technological process of identifying crisis situations in natural language processing. For example, the machine learning classifier can be trained to identify crisis situations that an individual setting up the system might not have predicted, while the RegEx classifier can ensure certain known or predicted phrases or inputs are properly classified even if they would not trigger the machine learning classifier.

These illustrative examples are given to introduce the reader to the general subject matter discussed here and are not intended to limit the scope of the disclosed concepts. The following sections describe various additional features and examples with reference to the drawings in which like numerals indicate like elements, and directional descriptions are used to describe the illustrative embodiments but, like the illustrative embodiments, should not be used to limit the present disclosure. The elements included in the illustrations herein may not be drawn to scale.

FIG. 1 is a schematic diagram depicting a computing environment 100 according to certain aspects of the present disclosure. The environment 100 can be located in a single physical location or can be distributed about multiple physical locations. Environment 100 can be used to implement an NLP system, such as being used to receive input phrases, process the input phrases to determine whether or not a crisis situation exists, and take any necessary actions, such as described in further detail herein. Environment 100 is an example of a suitable environment for implementing the NLP system, although other environments can be used instead.

Environment 100 can include a user device 102, a communication device 108, and a server 106, although in some cases one or two of these devices may not be included. For example, some environments contain only a user device 102, and some environments contain only a user device 102 and a communication device 108. In some cases, multiple user devices 102 can be used. In some cases, other devices can be used. When multiple devices are used, each device can be communicatively coupled together, such as via a direct connection (e.g., a wired connection, such as a universal serial bus (USB) connection, or a wireless connection, such as a Bluetooth connection) or via network 110. Network 110 can be any suitable network, such as a local area network, a wide area network, a cloud, or the Internet.

An individual can provide an input phrase to the NLP system, which can then process the input phrase to determine whether or not a crisis situation exists. The NLP system can be implemented on a single device (e.g., on user device 102) or can be implemented across multiple devices (e.g., any combination of user device 102, communication device 108, and sever(s) 106).

The NLP system can process the input phrase by applying a pattern matching classifier and a trained machine learning classifier. Each classifier can have classifier parameters that define how the classifier functions. In an example, the pattern matching classifier's classifier parameters can include matching criteria (e.g., a set of regular expressions containing one or more regular expressions), which can be configured to trigger whenever certain trigger phrases (e.g., triggering words, triggering collections of words, triggering symbols, triggering patterns of words, or the like) are present (e.g., matched) in the input phrase. In another example, the trained machine learning classifier's classifier parameters can include a model (e.g., a transformer model) that has already been trained for the purpose of identifying crisis situations.

When a crisis situation is detected, the NLP system can request confirmation from the individual (e.g., a user who provided the input phrase) or from another individual (e.g., a caregiver of medical professional treating a patient who provided the input phrase), who can provide a confirmation response that is either a confirmation or a denial of the crisis situation.

The NLP system can execute an abatement protocol, such as if the crisis situation is confirmed, which can involve communicating information to the individual, facilitating communication between the individual and another, providing one or more prompts to the user, providing one or more crisis management tools to the user, or otherwise engaging the user. In some cases, the NLP system can present a denial prompt to the user when the crisis situation is denied. The denial prompt can be used to discuss the trigger phrase with the user. Requesting confirmation, executing an abatement protocol, and/or presenting the denial prompt can be performed using any suitable component or combination of components of environment 100, such as the user device 102, the communication device 108, and server(s) 106.

A user device 102 can act as a primary mode of interaction for one or more individuals to provide input phrases, receive prompts and information, and otherwise interact with the NLP system. Examples of user device 102 include any suitable computing device, such as a personal computer, a smartphone, a tablet computer, a smartwatch, a computerized audio recorder, or the like. User device 102 can be operatively coupled to storage 104 to store data associated with applications and processes running on the user device 102. User device 102 can include any combination of input/output (I/O) devices that may be suitable for interacting with the NLP system, such as a keyboard, a mouse, a display, a touchscreen, a microphone, a speaker, an inertial measurement unit (IMU), a haptic feedback device, or other such devices.

A communication device 108 can be used to bridge the NLP system with a separate communication system, such as a telephone system. In some cases, communication device 108 can be used to provide input phrases to the NLP system. In some cases, communication device 108 can be used in the execution of an abatement protocol, such as to facilitate initiation of a communication between the user device 102 and an emergency service provider (e.g., a crisis support hotline). In some cases, however, user device 102 can act as a communication device 108.

One or more servers 106 can be used to process input phrases, such as input phrases received from user device 102 via network 110, and take further action (e.g., execute an abatement protocol or present a denial prompt). In some cases, server(s) 106 can receive an indication that a crisis situation has been detected (e.g., from a user device 102), then facilitate taking further action (e.g., by transmitting appropriate emergency information to user device 102 or by facilitating an emergency contact connection, such as via communication device 108).

In some cases, server(s) 106 can be used to receive information that can be used to update one or both of the classifiers. For example, server(s) 106 can receive a confirmation response and optionally an associated classifier (e.g., the triggering classifier that prompted the confirmation prompt) and/or an associated trigger phrase. This information can be used to automatically or manually update classifier parameters and improve one or both classifiers. For example, if the pattern matching classifier regularly identifies a particular phrase as indicative of a crisis situation, but individuals regularly provide confirmation responses that are denials, the matching criteria of the pattern matching classifier can be modified to no longer trigger based on the particular phrase. In another example, confirmation responses associated with a trigger phrase (e.g., the input phrase) can be used to improve training of the trained machine learning classifier's model. Even in cases where no trigger phrase is associated with the confirmation response, a confirmation response associated with the triggering classifier can help improve calculation of the particular classifier's operational statistics, including the classifier's accuracy, sensitivity, specificity, precision, and/or F-score. Calculation of such operational statistics can inform the need for updates or further training.

In some cases, classifying an input phrase can occur directly on the user device 102, such as using classifiers and/or classifier parameters stored in storage 104. In some cases, classifying an input phrase can occur at server(s) 106, with the user device 102 providing the input phrase to the server(s) 106. In some cases, classifying an input phrase can be split, with one classifier (e.g., the pattern matching classifier) running on the user device 102, and the second classifier (e.g., the trained machine learning classifier) running on the server(s) 106. In such cases, the user device 102 may be able to handle classification locally if the first classifier determines that the input phrase is associated with a crisis situation.

Figure 2:
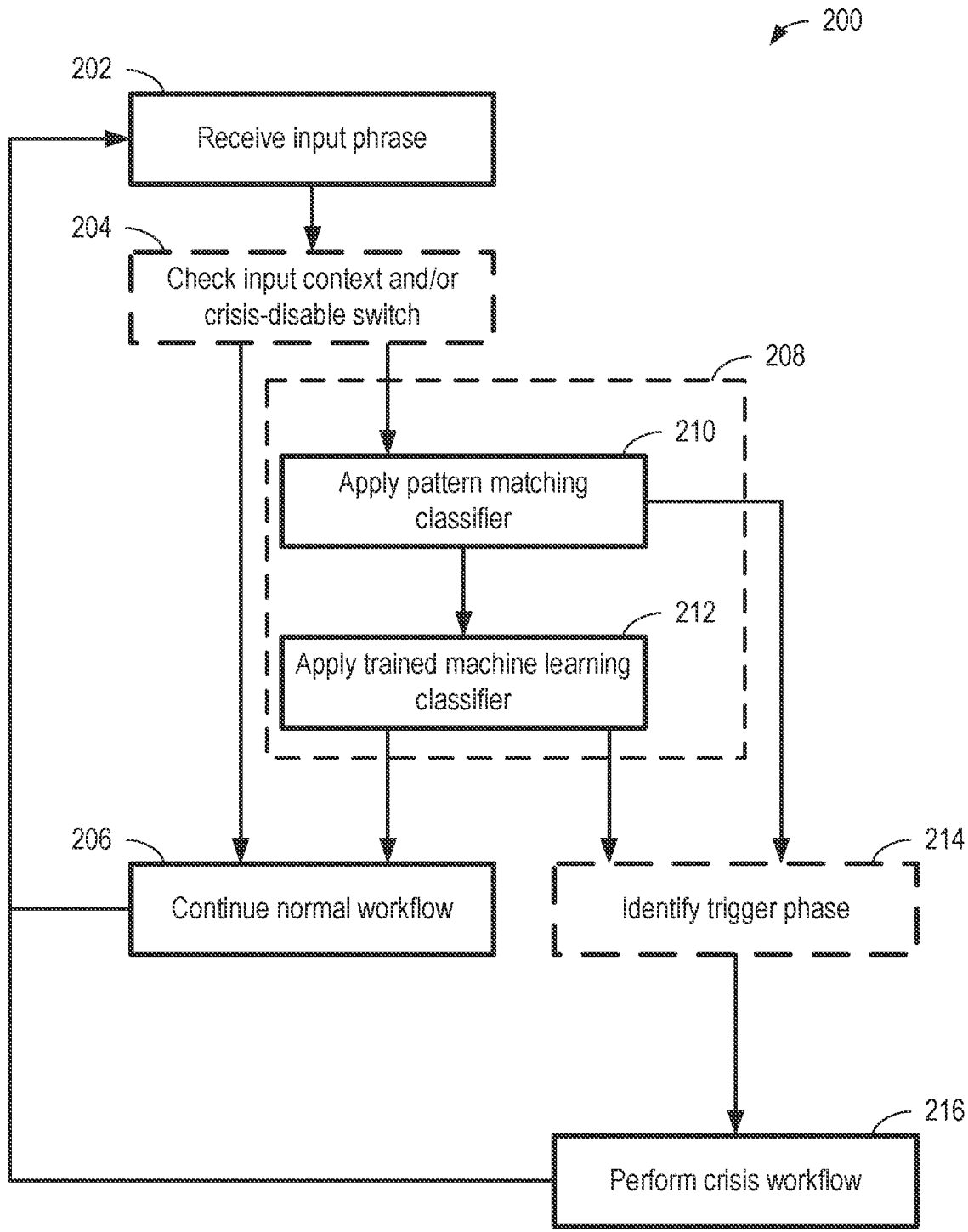
FIG. 2 is a flowchart depicting a process for identifying a crisis situation according to certain aspects of the present disclosure.

FIG. 2 is a flowchart depicting a process 200 for identifying a crisis situation according to certain aspects of the present disclosure. Process 200 can be performed by an NLP system in any suitable environment, such as environment 100 of FIG. 1. Process 200 can be repeated any number of times, such as once for each time the user provides an input phrase.

At block 202, an input phrase can be received. The input phrase can be a single character (e.g., a single symbol or emoticon), multiple characters, a single word, multiple words, an ordered string of words, a sentence, multiple sentences, or the like. In some cases, receiving an input phrase at block 202 can include concatenating multiple text entries, such as if an individual types and sends multiple messages in a row using a chatbot interface.

At optional block 204, the input context can be checked and/or a crisis-disable switch can be checked. Checking input context can be a useful tool to avoid invoking the crisis-checking classifiers when they may not be needed, such as if an individual is intentionally using input phrases that would normally trigger a finding of a crisis situation as an example or in a tool where the individual is instructed to provide certain phrases that may otherwise normally trigger a finding of a crisis situation. Checking input context can include identifying a context associated with receiving the input, such as identifying a particular tool or application being used to provide the input, or phrases that otherwise indicate the input phrase should not invoke the crisis-checking classifiers. Depending on the input context, the NLP system can either proceed with crisis checking at block 208, or can skip the crisis checking and instead continue the normal workflow at block 206.

In some cases, at optional block 204, a crisis-disable switch can be checked. The crisis-disable switch can be a physical or digital switch or setting that permits input phrases to be received without being checked by one, some, or all the crisis-checking classifiers. In some cases, the crisis-disable switch can be automatically triggered, such as based on input context or in response to a denial of a crisis situation associated with a recent input phrase triggering a crisis-checking classifier.

For a crisis-disable switch that is meant to disable all crisis-checking, when that crisis-disable switch is enabled, the received input phrase from block 202 will be processed according to the normal workflow at block 206. However, when the crisis-disable switch is disabled, the received input phrase from block 202 will be processed normally by the crisis-checking classifiers at block 208. In some cases, the crisis-disable switch can be designed to disable at least one, but fewer than all of the crisis-checking classifiers. For example, the crisis-disable switch can be designed to disable the trained machine learning classifier, thus only using the pattern matching classifier to perform crisis-checking. In such an example, crisis-matching can be turned off for everything except for certain critical input phrases that would be matched by the pattern matching classifier. In some cases, when the crisis-disable switch is enabled, alternate classifier parameters can be used by one or more of the classifiers. For example, when the crisis-disable switch is enabled, the pattern matching classifier may use alternate classifier parameters that only match for a relatively small set of input phrases as compared to the classifier parameters when the crisis-disable switch is not enabled.

Continuing the normal workflow at block 206 can include processing the input phrase as it would otherwise be processed without crisis checking. For example, in the case of an artificial intelligence chatbot, continuing normal workflow may include processing the input phrase through one or more additional classifiers, and otherwise processing the input phrase to determine a response to give, then providing that response. As part of or after completing the normal workflow at block 206, process 200 can repeat whenever another input phrase is received at a new instance of block 202.

In some cases, continuing the normal workflow at block 206 can include accessing memory to determine if an immediately prior conversation was associated with a past crisis situation or associated with interactions immediately following such a past crisis situation (e.g., interactions in response to or during execution of the abatement protocol). If the immediately prior conversation was indeed associated with a past crisis situation or with interactions immediately following such a past crisis situation, the NLP system can present a prompt to the user that is related to that past crisis situation (e.g., a request to see how the individual is feeling now that time has elapsed since the crisis situation or a request to see how the individual ended up handling the crisis situation).

At block 208, the input phrase can be processed by the crisis-checking classifiers. When input context is checked and/or a crisis-disable switch is checked at block 204, the input phrase from block 202 may only be processed by the crisis-checking classifier at block 208 if it is determined at block 204 that the crisis-checking classifier should be used. However, in some cases, the input phrase received at block 202 is automatically processed by the crisis-checking classifiers at block 208. In some cases, the input phrase received at block 202 can be processed by the crisis-checking classifiers at block 208 before it is processed by any other classifiers associated with generating a response to the input phrase.

At block 208, the input phrase can be classified by two classifiers. While depicted in a particular sequential order in FIG. 2, the two classifiers can be applied in other orders or simultaneously. At block 21, a pattern matching classifier is applied to the input phrase from block 202. Applying the pattern matching classifier at block 210 can include processing the input phrase using the pattern matching classifier to determine whether or not the input phrase is indicative of a crisis situation. Applying the pattern matching classifier at block 210 can include searching the input phrases using a set of matching criteria, which can include one or more criterion. In some cases, applying the pattern matching classifier at block 210 can include accessing the matching criteria, such as from a local memory or via the Internet. Applying the pattern matching classifier at block 210 can result in the pattern matching classifier triggering or not triggering. If the input phrase matches any inclusionary matching criteria, taking in account exclusionary matching criteria, if any, the classifier can deem the input phrase as being indicative of a crisis situation, and can be triggered. If the pattern matching classifier does not trigger when processing the input phrase (e.g., the input phrase does not match or is excluded based on the matching criteria), the input phrase can be outputted to the trained machine learning classifier or the trained machine learning classifier can be otherwise signaled to start processing the input phrase.

At block 212, the trained machine learning classifier can be applied to the input phrase as received from the pattern matching classifier from block 210. Applying the trained machine learning classifier at block 210 can include processing the input phrase using the trained machine learning classifier to determine whether or not the input phrase is indicative of a crisis situation. Applying the trained machine learning classifier at block 212 can include accessing a model associated with the trained machine learning classifier and applying the input phrase to the model. In some cases, the model can be accessed from a local memory or via the Internet. Applying the trained machine learning classifier at block 210 can result in the trained machine learning classifier triggering or not triggering. If the results of the trained machine learning classifier indicate the input phrase is indicative of a crisis situation, the trained machine learning classifier will trigger. If the results of the trained machine learning classifier indicate that the input phrase is not indicative of a crisis situation, the input phrase can be passed to the normal workflow at block 206 or the trained machine learning classifier can otherwise signal to the NLP system to continue processing the input phrase under the normal workflow at block 206. The trained machine learning classifier can be trained using training data including a set of input phrases, the set of input phrases including a subset of input phrases associated with a crisis situation and a subset of input phrases not associated with a crisis situation.

In some optional cases, if either the pattern matching classifier from block 210 or the trained machine learning classifier from block 212 are triggered, the trigger phrase can be identified at block 214. A trigger phrase can be a portion of or an entirety of the input phrase from block 202. In cases where the pattern matching classifier is triggered at block 210, identifying the trigger phrase can include identifying, as the trigger phrase, either the entire input phrase or the portion of the input phrase that matched the matching criteria of the pattern matching classifier. In cases where the trained machine learning classifier is triggered at block 212, identifying the trigger phrase can include identifying the entire input phrase as the trigger phrase. In some cases, identifying the trigger phrase associated with triggering of a trained machine learning classifier can include determining contribution values for portions of the input phrase and selecting as the trigger phrase the portions of the input phrase having contribution values over a threshold (e.g., a static or dynamic threshold).

In response to either the pattern matching classifier from block 210 or the trained machine learning classifier from block 212 being triggered, the crisis workflow can be performed at block 216. Performing the crisis workflow can include optionally confirming the crisis situation, executing an abatement protocol, presenting any denial prompts, or otherwise interacting with the individual in association with the crisis situation. In some cases, performing the crisis workflow at block 216 can include making use of the trigger phrase identified at block 214. In some cases, performing the crisis workflow at block 216 can include making use of an indication of which classifier was triggered.

Process 200 is depicted with a certain arrangement of blocks, however in other cases, these blocks can be performed in different orders, with additional blocks, and/or some blocks removed. For example, in some cases, the input phrase can be first provided to a trained machine learning classifier before being provided to a pattern matching classifier.

Figure 3:
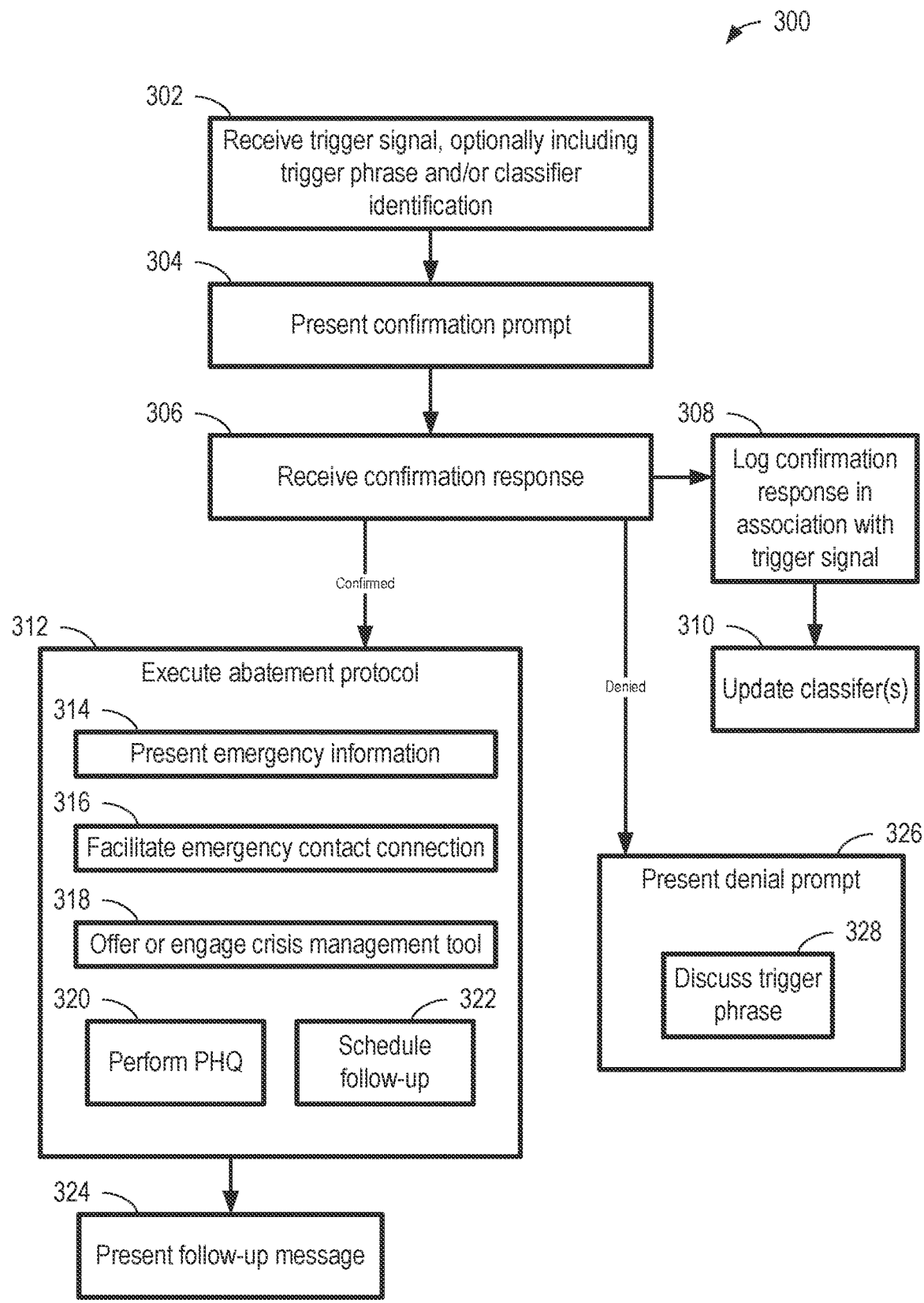
FIG. 3 is a flowchart depicting a process for confirming and responding to a crisis situation according to certain aspects of the present disclosure.

FIG. 3 is a flowchart depicting a process 300 for confirming and responding to a crisis situation according to certain aspects of the present disclosure. Process 300 can be performed by an NLP system in any suitable environment, such as environment 100 of FIG. 1. Process 300 can represent performing a crisis workflow, such as performed with respect to block 216 of FIG. 2.

At block 302, a trigger signal can be received. The trigger signal can be generated by or in response to a classifier determining that a particular input phrase is indicative of a crisis situation. In some cases, receiving the trigger signal at block 302 can include receiving a trigger phrase (e.g., a trigger phrase as identified at block 214 of FIG. 2). In some cases, receiving the trigger signal at block 302 can include receiving a classifier identification. The classifier identification can be information usable to identify which classifier or which type of classifier was triggered.

At block 304, a confirmation prompt is presented. Presentation of the confirmation prompt can include asking the individual if they are undergoing a crisis situation. In some cases, the confirmation prompt can be presented to someone other than the individual who provided the input phrase, such as if a caregiver or therapist is interacting with the individual, in which case the caregiver or therapist may be provided with a confirmation prompt indicating that the individual may be suffering from a crisis situation.

In some cases, presenting the confirmation prompt at block 304 can include presenting an explanation that the crisis workflow was triggered and/or presenting the trigger phrase or the input phrase. In an example of an input phrase of "I want to kill myself." the NLP system may identify the phrase as matching the matching criteria of the pattern matching classifier with a trigger phrase of "want to kill," then the NLP system can present a confirmation prompt that includes "My crisis systems have been triggered. This is because I've recognized "want to kill" as an emergency. Is this the case? Are you in crisis?" Other examples can be used. In some cases, presenting the confirmation prompt at block 304 can include presenting a set of options from which the individual may select a response (e.g., "Yes" or "No"). In some cases, presenting the confirmation prompt at block 304 can include requesting confirmation in an open format (e.g., allowing a user to type in their own response rather than selecting from a set of options).

At block 306, a confirmation response can be received. The confirmation response is received in response to the confirmation prompt. In some cases, the confirmation response can be one of a set of options provided at block 304. In some cases, the confirmation response can be initially provided in the form of an input phrase (e.g., text input), which the NLP system can analyze to classify as appropriate (e.g., a confirmation of the crisis situation or a denial of the crisis situation, or optionally a request for more information). Generally, a confirmation response will be indicative of a confirmation of the crisis situation or a denial of the crisis situation, although that need not always be the case.

In some optional cases, depending on the input phrase used, block 304 can be skipped and the trigger signal itself can be considered a confirmation response that confirms the crisis situation. For example, an input phrase that explicitly states the individual is in a crisis or explicitly requests crisis aid, the NLP system may automatically assume that the input phrase itself is a confirmation response that confirms the existence of a crisis situation.

At block 308, the confirmation response can be logged in associated with the trigger signal. Logging the confirmation response in association with the trigger signal can include transmitting and/or storing data indicative of the confirmation response in association with the trigger signal. The trigger signal can include an indication of the input phrase, an indication of the trigger phrase, an indication of why the trigger signal was generated (e.g., which classifier was triggered), or other such information. Logging the confirmation response in association with the trigger signal can include logging the confirmation response in association with at least a portion of the trigger signal. For example, in some cases, the confirmation response may be logged with just the trigger phrase. In another example, the confirmation response may be logged with the input phrase and an indication of which classifier was triggered. In another example, the confirmation response may be logged with the input phrase and the trigger phrase. In such an example, knowledge of the input phrase and the trigger phrase may be usable to discern which classifier was triggered in cases where the trained machine learning classifier always uses the entire trigger phrase as the input phrase and the pattern matching classifier always uses a portion of the trigger phrase as the input phrase.

At block 310, one or both of the classifiers can be updated using the logged confirmation response. In some cases, updating a classifier using the logged confirmation response can include preparing updated performance statistics associated with the classifier that include the logged confirmation response. Such updated performance statistics can be used to inform an update to the classifier. In some cases, updating a classifier using the logged confirmation response can include using the logged confirmation response as training data (e.g., as a data point in a larger set of training data). Using the logged confirmation response as training data can include adding the logged confirmation response to an existing set of training data, then using that set of training data to initially train a machine learning model (e.g., a model of the trained machine learning classifier) or to update (e.g., fine-tune) training of an existing machine learning model (e.g., an existing model of the trained machine learning classifier, such as a pretrained model).

When the NLP system assumes or knows that a crisis situation exists (e.g., via receiving a confirmation of the crisis situation at block 306), the process 300 can continue at block 312 with executing an abatement protocol. Executing the abatement protocol can include performing or initiating the performance of one or more actions that are designed or selected to help mitigate the crisis situation or otherwise aid the individual in managing the crisis situation. Such actions can be known as mitigation actions. Executing the abatement protocol can include performing actions in any suitable order, including simultaneously, as appropriate. In some cases, executing the abatement protocol at block 312 can include accessing preset data (e.g., text strings, such as phrases; computer links, such as hyperlinks; images; or other content) and presenting that preset data (e.g., sending the preset data such that the preset data, when received, is displayed on a display device). In some cases, the preset data can include comforting or sympathetic phrases, images, or other content.

In some cases, executing an abatement protocol at block 312 can include presenting emergency information at block 314. Presenting emergency information can include accessing data associated with the emergency information (e.g., a text string containing emergency contact information) and sending the data such that the data, when received, is displayed on a display device or otherwise provided to the user in a comprehensible fashion (e.g., via text printed by printer or audio signals generated by a speaker). Presenting emergency information can include presenting preset emergency information, such as a preset list of emergency contact phone numbers or websites, preset instructions for managing the crisis situation, or other such emergency information. In some cases, presenting emergency information at block 314 can include accessing emergency information, such as from memory or from the Internet (e.g., a server on the Internet). In some cases, accessing emergency information can include providing information associated with the individual and/or information associated with the trigger signal, which information can be used to obtain relevant emergency information that can then be presented. In an example, a geolocation of the individual (e.g., based on a geolocation of a user device, a preset location, or one or more sensors of a user device) can be used to obtain emergency information associated with that geolocation (e.g., emergency information for a particular county, city, state, country, or the like). In another example, information about the trigger signal can be used to select appropriate emergency information suitable for the type of crisis situation at hand.

In some cases, executing an abatement protocol at block 312 can include facilitating an emergency contact connection at block 316. Facilitating an emergency contact connection can include presenting an option or prompt to make an emergency contact connection and/or automatically making an emergency contact connection. For example, in some cases, facilitating an emergency contact connection can include accessing and presenting a link configured to begin initiation of an emergency contact connection upon actuation. Beginning initiation of an emergency contact connection can include taking initial step(s) to start the connection (e.g., opening a telephone app on a smartphone and pre-populating the dial field with an emergency contact phone number without starting the phone call) or can include taking all step(s) to start the connection (e.g., opening a telephone app on a smartphone and automatically dialing the emergency contact phone number). Such a link can be a link to begin initiation of a telephone call, a link to begin initiation of a videoconference, a link to begin initiation of a text chat, a link to begin initiation of a text message or similar message, or other such links. In another example, in some cases, facilitating an emergency contact connection can include sending a signal to automatically begin initiation of an emergency contact connection (e.g., automatically start up a telephone app and prepopulate the given phone number without starting the call or automatically start up a telephone app and call the given phone number). Such a signal can include a signal to automatically begin initiation of a phone call, a signal to automatically begin initiation of a videoconference, a signal to automatically begin initiation of a text chat, a signal to automatically begin initiation of a text message, or the like. In some cases, actuation of a link to begin initiation of a given action can result in sending the signal to automatically begin initiation of that action. In some cases, beginning initiation of an action can be performed by the user's device or another device associated with the user (e.g., another device owned by the user and/or assigned to an account or unique identifier of the user). In some cases, however, beginning initiation of an action can be performed by a remote device. For example, in some cases, beginning initiation of a phone call can include sending a command to a remote system to place a call to the user's phone number.

An emergency contact connection can be an audio connection (e.g., a telephone call), a video connection (e.g., a videoconference call), a text-based connection (e.g., a text message or chat message communication), or other such connections. In some cases, facilitating the emergency contact connection can include making an emergency contact connection using the emergency information presented at block 314, although that need not always be the case. In some cases, facilitating the emergency contact connection can include beginning to initiate or automatically initiating an emergency contact connection with a preset party (e.g., a family member or caregiver previously selected by the individual).

In some cases, executing an abatement protocol at block 312 can include offering or engaging a crisis management tool at block 318. Offering a crisis management tool can include generating a prompt that can be presented to a user, the response to which can be used to select one or more crisis management tools and optionally initiate the selected crisis management tool. Engaging a crisis management tool can include automatically initiating the crisis management tool. A crisis management tool can be a workflow of prompts and/or comments used to engage the individual in a fashion that may help mitigate the crisis situation. In an example, a crisis management tool can be a list of actions or tasks to be accomplished, which can be selected to help mitigate the crisis situation. In another example, a crisis management tool can be a series of questions that can help the individual identify a cause of the crisis situation and hopefully better manage the cause of the crisis situation. In some cases, one or more crisis management tools are offered at block 318, allowing the individual to select a particular crisis management tool to use or optionally decline the crisis management tool(s). In some cases, a crisis management tool can be automatically engaged at block 318.

In some cases, executing an abatement protocol at block 312 can include performing a patient health questionnaire (PHQ) at block 320. Performing a PHQ can include initiating a PHQ protocol to access and present one or more questions associated with the PHQ. In some cases, the PHQ protocol can include selecting a particular PHQ to be performed from a set of PHQs. The PHQ protocol can include stored and/or transmitting result data. The result data of the PHQ protocol can include individual answers to questions, individual or cumulative scores, and/or other metrics associated with performance of the PHQ (e.g., reaction time to answer a questions, time of day, and the like). In some cases, results (e.g., result data) from performing a PHQ during a crisis situation can be a useful metric to have. Performing the PHQ can include storing the responses, optionally in association with an indicator that the PHQ was taken during a crisis situation. Any suitable PHQ can be used, although use of the Patient Health Questionnaire-2 (PHQ-2) can be especially useful for certain aspects of the present disclosure, as it provides useful information while remaining short and easy to answer, allowing other actions of the abatement protocol to be quickly performed. Performing the PHQ-2 can include asking the individual to provide rankings (e.g., "Not at all," "Several days," "More than half the days," and "Nearly every day") to questions about whether the individual has been bothered in the past two weeks by i) little interest or pleasure in doing things; and ii) feeling down, depressed, or hopeless.

In some cases, executing an abatement protocol at block 312 can include scheduling a follow-up at block 322. Scheduling a follow-up can include establishing a time (e.g., a date and time of day) for a follow-up or a duration of time (e.g., a number of hours, days, or the like) that must elapse before a follow-up should occur. In some cases, scheduling a follow-up at block 322 can be automatically performed using a preset time offset (e.g., automatically set for today's date+48 hours) or a preset value (e.g., automatically set for no earlier than 48 hours from now). In some cases, scheduling a follow-up at block 322 can include presenting a prompt offering a number of preset options for a follow-up. In some cases, scheduling a follow-up at block 322 can include presenting a prompt requesting the individual provide a time or a duration of time for the follow-up.

At block 324, the NLP system can present a follow-up message. The follow-up message can be presented based on the schedule defined at block 322, or automatically. In some cases, presenting the follow-up message at block 324 can occur minutes, hours, days, or weeks after execution of the abatement protocol at block 312. Presenting the follow-up message can include presenting a prompt seeking information about the individual, such as whether or not the crisis situation is ongoing or how the individual managed the crisis situation. In some cases, presenting the follow-up message can include performing a subsequent PHQ and optionally comparing it to a PHQ performed at block 320.

In some cases, when a confirmation response received at block 306 is a denial of the crisis situation, process 300 can end, permitting the NLP system to proceed with the normal workflow. However, in some cases, when a confirmation response received at block 306 is a denial of the crisis situation, the NLP system can present a denial prompt at 326. Presenting the denial prompt can include presenting a prompt to elicit additional information about why the detected crisis situation was not a crisis situation according to the individual. In some cases, presenting the denial prompt at block 326 includes using the trigger phrase, such as to discuss the trigger phrase at block 328. Discussing the trigger phrase can include presenting prompts and/or comments to understand why the detected crisis situation was not actually a crisis situation according to the individual. In some cases, presenting the denial prompt at block 326 can include logging the response to the denial prompt. In some cases, the logged response to the denial prompt can be used to further update one or both classifiers, such as to inform a developer as to how to configure or train one or both of the classifiers to try and avoid triggering when the individual is likely, certain, or nearly certain to deny that a crisis situation has occurred.

In some cases, when a confirmation response received at block 306 is a denial of the crisis situation, the NLP system can present the denial prompt at block 326, then proceed to nevertheless executing the abatement protocol at block 312 or a modified version thereof, such as executing a modified abatement protocol that takes into account that the individual has denied the existence of a crisis situation. For example, such a modified abatement protocol may include actions that are designed to mitigate a crisis situation but not outwardly imply or acknowledge the existence of a crisis situation (e.g., asking questions to help calm or ground an individual without specifically noting that a crisis situation is occurring).

Process 300 is depicted with a certain arrangement of blocks, however in other cases, these blocks can be performed in different orders, with additional blocks, and/or some blocks removed. For example, in some cases, process 300 can proceed without presenting a confirmation prompt or receiving a confirmation response, in which case the abatement protocol can be executed at block 312 in response to receiving the trigger signal at block 302. In another example, process 300 may end after presentation of the confirmation prompt at block 304. In another example, process 300 may include only blocks 302, 304, 306, 308, and 310.

Figure 4:
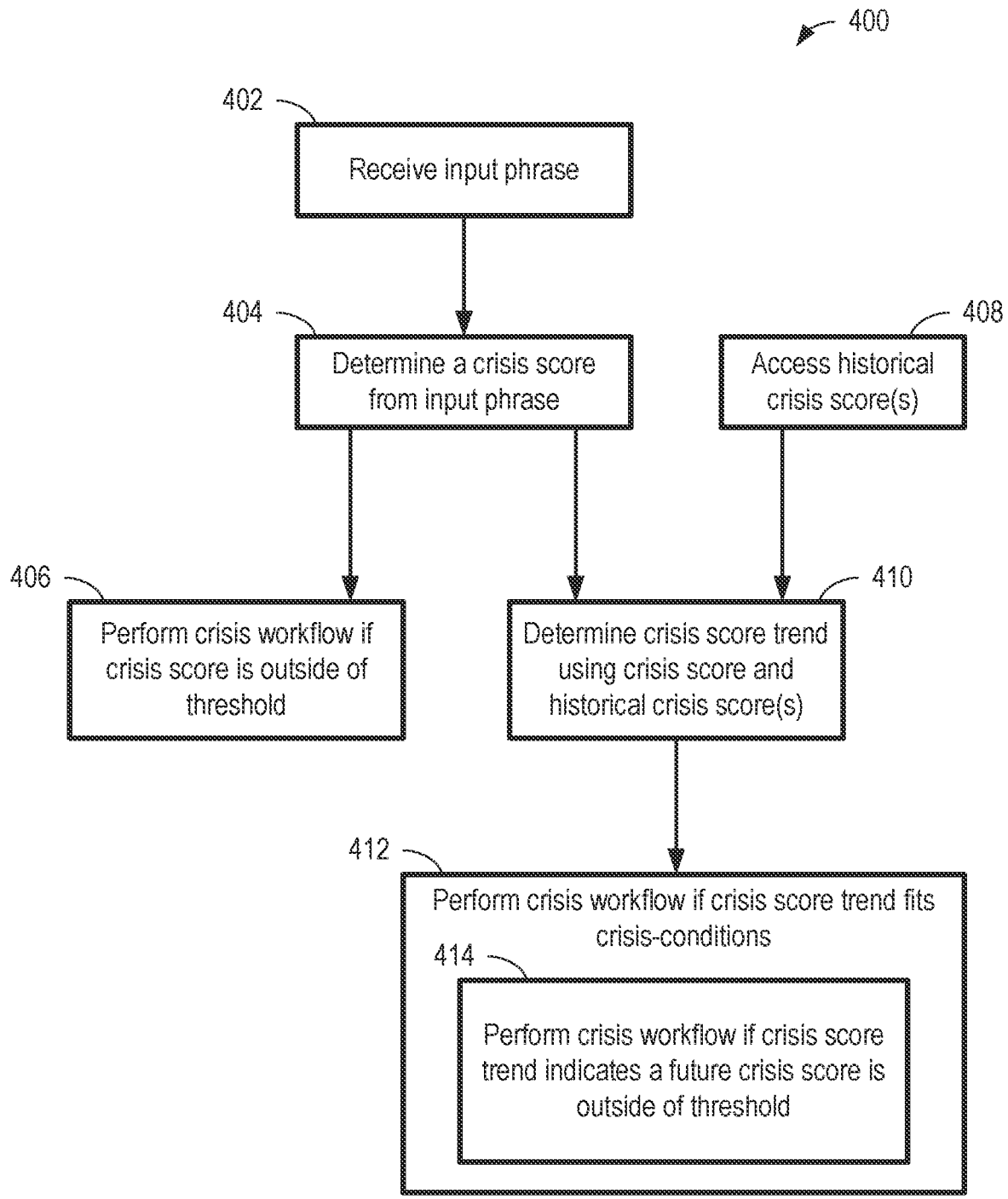
FIG. 4 is a flowchart depicting a process for quantifying and identifying a crisis situation according to certain aspects of the present disclosure.

FIG. 4 is a flowchart depicting a process 400 for quantifying and identifying a crisis situation according to certain aspects of the present disclosure. Process 400 can be performed by an NLP system in any suitable environment, such as environment 100 of FIG. 1. Process 400 can be repeated any number of times, such as once for each time the user provides an input phrase.

At block 402, an input phrase is provided. Providing an input phrase at block 402 can be similar to providing an input phrase at block 202 of FIG. 2.

At block 404, a crisis score can be determined from the input phrase. In some cases, determining a crisis score can include performing a classification using one or both of a pattern matching classifier and a trained machine learning classifier. In some cases, the pattern matching classifier and trained machine learning classifier can be configured to output tiers or a numerical value associated with whether or not the input phrase is likely to indicate a crisis situation. The output from one or both classifiers can be used as a crisis score or a component for a crisis score (e.g., the component score from each classifier can be added together and/or averaged for a total crisis score). In an example, a pattern matching classifier may output a component score by outputting a score of 0 for no matches, a score of 1 for matches according to a first set of matching criteria, and a score of 2 for matches according to a second set of matching criteria, and a score of 3 for matches according to both the first set of matching criteria and the second set of matching criteria. Any number of scores can be used and any number or combination of sets of matching criteria can be used. In another example, the trained machine learning classifier can be configured and trained to output scores (e.g., from 0 to 10) based on an increasing likelihood that the input phrase indicates a crisis situation.

In some cases, process 400 can continue at block 406 by performing a crisis workflow if the crisis score determined at block 404 is outside of a certain threshold. Being outside of a threshold can include being below a threshold value, being above a threshold value, or being between a lower threshold value and a higher threshold value. The threshold can be a preset number, although that need not always be the case. In some cases, the threshold can be adjusted based on confirmation responses from previous instances of the crisis workflow. For example, if a threshold is set at 5, but previous instance(s) of the crisis workflow being triggered due to a score of 6 have resulted in a confirmation response that is a denial of the crisis situation, the threshold may be automatically or manually adjusted upwards, such as to 6 or 7. Other adjustments can be made.

In some cases, instead of or in addition to block 406, the decisions to perform (e.g., trigger) a crisis workflow can be based on one or more historical crisis scores. At block 408, one or more historical crisis scores can be accessed. The historical crisis scores that are accessed can be based on a number of scores (e.g., the previous 10 scores), a duration of time (e.g., any scores in the past 8 weeks), or otherwise (e.g., all scores or all scores with similar input phrases).

At block 410, a crisis score trend can be determined based on the crisis score from block 404 and the historical crisis score(s) from block 408. In some cases, the crisis score trend can be an average of the crisis score and historical crisis scores. In some cases, the crisis score trend can be a mathematical trend, such as a mathematical trend that can be expressed as a function of sequence or time. For example, several historical crisis scores and the crisis score may exhibit an upward trend (e.g., increasing 1-2 points per day or per sequential crisis score). Such a mathematical trend can be determined through any suitable technique.

At block 412, the crisis workflow can be performed (e.g., triggered) if the crisis score trend fits one or more crisis-conditions. An example of a crisis-condition can be a particular number of days or sequential crisis scores in sequence showing an increasing crisis score. In another example, a crisis-condition can be a particular slope associated with a crisis score trend (e.g., a trend showing large consecutive increases in crisis score, even if the crisis score itself remains below a threshold level). In some cases, the crisis-condition occurs when the crisis score trend indicates that a future crisis score (e.g., a subsequent crisis score, a crisis score after a given period of time (e.g., a day), or a crisis score within a given period of time (e.g., a week)) will be outside of a threshold.

Performing the crisis workflow at blocks 406, 412, or 414 can include performing any suitable crisis workflow, such as some or all of process 300 of FIG. 3. In some cases, one or more trigger phrases that contributed to the crisis score can be provided to the crisis workflow as part of a trigger signal. In some cases, only one or more trigger phrases that contributed most to the crisis score will be provided.

Process 400 is depicted with a certain arrangement of blocks, however in other cases, these blocks can be performed in different orders, with additional blocks, and/or some blocks removed. For example, in some cases, process 400 can proceed without block 406. In another example, process 400 can proceed without blocks 408, 410, 412, and 414.

Figure 5:
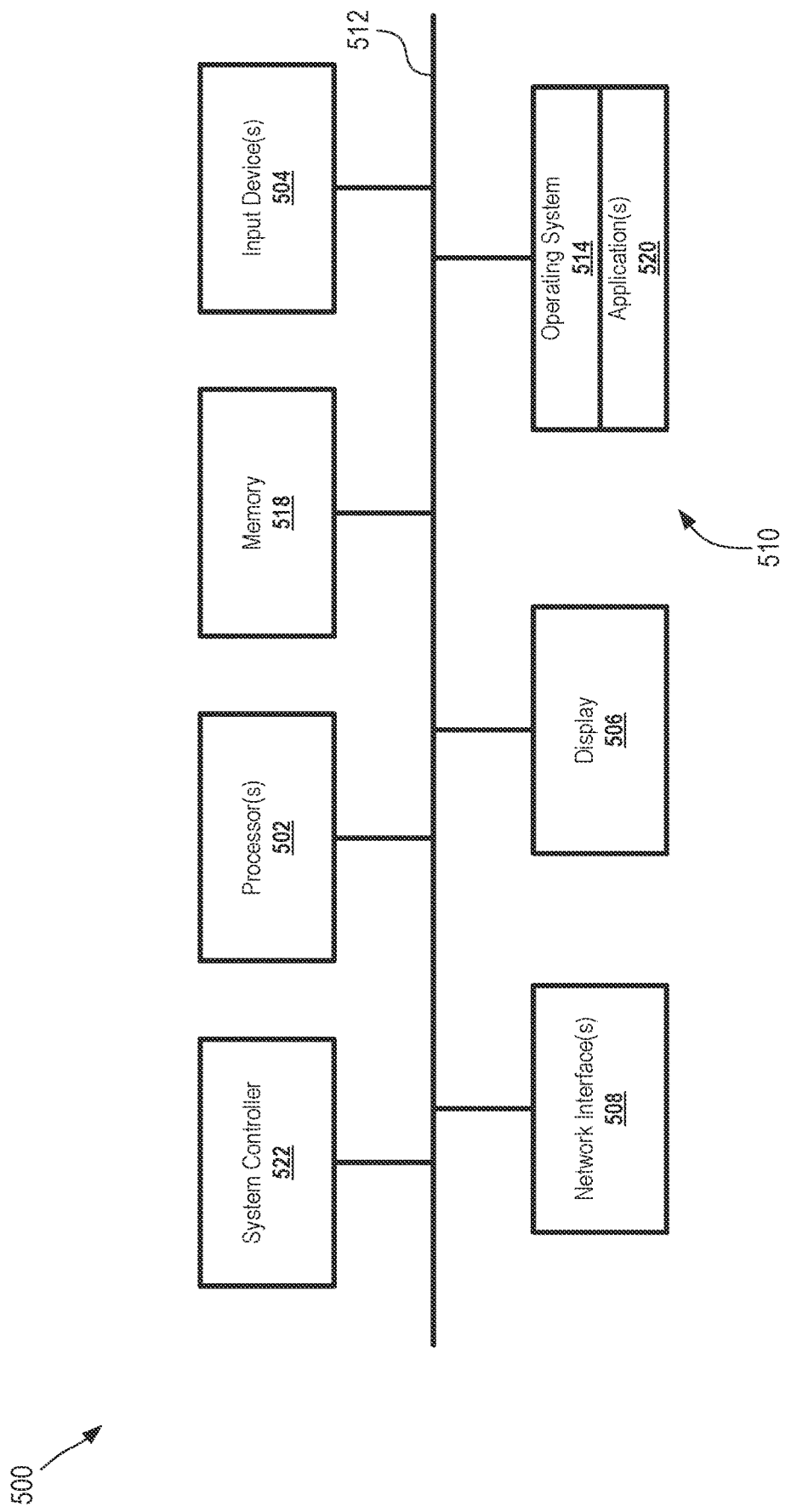
FIG. 5 is a block diagram depicting an example system architecture for implementing certain features and processes of the present disclosure

FIG. 5 is a block diagram of an example system architecture 500 for implementing features and processes of the present disclosure, such as those presented with reference to processes 200, 300, and 400 of FIGS. 2, 3, and 4, respectively. The architecture 500 can be used to implement a server (e.g., server 106 of FIG. 1), a user device (e.g., user device 102 of FIG. 1), a communication device (e.g., communication device 112 of FIG. 1), or any other suitable device for performing some or all of the aspects of the present disclosure. The architecture 500 can be implemented on any electronic device that runs software applications derived from compiled instructions, including without limitation personal computers, servers, smart phones, electronic tablets, game consoles, email devices, and the like. In some implementations, the architecture 500 can include one or more processors 502, one or more input devices 504, one or more display devices 506, one or more network interfaces 508, and one or more computer-readable mediums 510. Each of these components can be coupled by bus 512.

Display device 506 can be any known display technology, including but not limited to display devices using Liquid Crystal Display (LCD) or Light Emitting Diode (LED) technology. Processor(s) 502 can use any known processor technology, including but not limited to graphics processors and multi-core processors. Input device 504 can be any known input device technology, including but not limited to a keyboard (including a virtual keyboard), mouse, track ball, and touch-sensitive pad or display. In some cases, audio inputs can be used to provide audio signals, such as audio signals of an individual speaking. Bus 512 can be any known internal or external bus technology, including but not limited to ISA, EISA, PCI, PCI Express, NuBus, USB, Serial ATA or FireWire.

Computer-readable medium 510 can be any medium that participates in providing instructions to processor(s) 502 for execution, including without limitation, non-volatile storage media (e.g., optical disks, magnetic disks, flash drives, etc.) or volatile media (e.g., SDRAM, ROM, etc.). The computer-readable medium (e.g., storage devices, mediums, and memories) can include, for example, a cable or wireless signal containing a bit stream and the like. However, when mentioned, non-transitory computer-readable storage media expressly exclude media such as energy, carrier signals, electromagnetic waves, and signals per se.

Computer-readable medium 510 can include various instructions for implementing operating system 514 and applications 520 such as computer programs. The operating system can be multi-user, multiprocessing, multitasking, multithreading, real-time and the like. The operating system 514 performs basic tasks, including but not limited to: recognizing input from input device 504; sending output to display device 506; keeping track of files and directories on computer-readable medium 510; controlling peripheral devices (e.g., storage drives, interface devices, etc.) which can be controlled directly or through an I/O controller; and managing traffic on bus 512. Computer-readable medium 510 can include various instructions for implementing firmware processes, such as a BIOS. Computer-readable medium 510 can include various instructions for implementing any of the processes described herein, including at least processes 200, 300, and 400 of FIGS. 2, 3, and 4, respectively.

Memory 518 can include high-speed random access memory and/or non-volatile memory, such as one or more magnetic disk storage devices, one or more optical storage devices, and/or flash memory (e.g., NAND, NOR). The memory 518 (e.g., computer-readable storage devices, mediums, and memories) can include a cable or wireless signal containing a bit stream and the like. However, when mentioned, non-transitory computer-readable storage media expressly exclude media such as energy, carrier signals, electromagnetic waves, and signals per se. The memory 518 can store an operating system, such as Darwin, RTXC, LINUX, UNIX, OS X, WINDOWS, or an embedded operating system such as VxWorks.

System controller 522 can be a service processor that operates independently of processor 502. In some implementations, system controller 522 can be a baseboard management controller (BMC). For example, a BMC is a specialized service processor that monitors the physical state of a computer, network server, or other hardware device using sensors and communicating with the system administrator through an independent connection. The BMC is configured on the motherboard or main circuit board of the device to be monitored. The sensors of a BMC can measure internal physical variables such as temperature, humidity, power-supply voltage, fan speeds, communications parameters and operating system (OS) functions.

The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language (e.g., Objective-C, Java), including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors or cores, of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computing system that includes a back-end component, such as a data server, or that includes a middleware component, such as an application server or an Internet server, or that includes a front-end component, such as a client computer having a graphical user interface or an Internet browser, or any combination thereof. The components of the system can be connected by any form or medium of digital data communication such as a communication network. Examples of communication networks include, e.g., a LAN, a WAN, and the computers and networks forming the Internet.

The computing system can include clients and servers. A client and server are generally remote from each other and typically interact through a network. The relationship of client and server arises by virtue of computer programs running on the respective computers and having a client-server relationship to each other.

One or more features or steps of the disclosed embodiments can be implemented using an application programming interface (API). An API can define one or more parameters that are passed between a calling application and other software code (e.g., an operating system, library routine, function) that provides a service, that provides data, or that performs an operation or a computation.

The API can be implemented as one or more calls in program code that send or receive one or more parameters through a parameter list or other structure based on a call convention defined in an API specification document. A parameter can be a constant, a key, a data structure, an object, an object class, a variable, a data type, a pointer, an array, a list, or another call. API calls and parameters can be implemented in any programming language. The programming language can define the vocabulary and calling convention that a programmer will employ to access functions supporting the API.

In some implementations, an API call can report to an application the capabilities of a device running the application, such as input capability, output capability, processing capability, power capability, communications capability, and the like.

The foregoing description of the embodiments, including illustrated embodiments, has been presented only for the purpose of illustration and description and is not intended to be exhaustive or limiting to the precise forms disclosed. Numerous modifications, adaptations, and uses thereof will be apparent to those skilled in the art. Numerous changes to the disclosed embodiments can be made in accordance with the disclosure herein, without departing from the spirit or scope of the invention. Thus, the breadth and scope of the present invention should not be limited by any of the above described embodiments.

Although the invention has been illustrated and described with respect to one or more implementations, equivalent alterations and modifications will occur or be known to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only, and is not intended to be limiting of the invention. As used herein, the singular forms "a," "an," and "the" are intended to include the plural forms as well, unless the context clearly indicates otherwise. Furthermore, to the extent that the terms "including," "includes," "having," "has," "with," or variants thereof, are used in either the detailed description and/or the claims, such terms are intended to be inclusive in a manner similar to the term "comprising."

As used below, any reference to a series of examples is to be understood as a reference to each of those examples disjunctively (e.g., "Examples 1-4" is to be understood as "Examples 1, 2, 3, or 4").

Example 1 is a system, comprising: one or more data processors; and a non-transitory computer-readable storage medium containing instructions which, when executed on the one or more data processors, cause the one or more data processors to perform operations including: receiving an input phrase associated with a crisis situation; applying a first classifier on the input phrase to determine that the input phrase does not trigger the first classifier; applying a second classifier on the input phrase to determine that the input phrase triggers the second classifier, wherein the first classifier is one of a pattern matching classifier and a trained machine learning classifier, and wherein the second classifier is the other of the pattern matching classifier and the trained machine learning classifier; generating a trigger signal in response to determining that the input phrase triggers the second classifier; and executing an abatement protocol in response to generation of the trigger signal, wherein execution of the abatement protocol is intended to mitigate the crisis situation.

Example 2 is the system of example(s) 1, wherein executing the abatement protocol includes i) accessing and presenting a text string containing emergency contact information, ii) accessing and presenting a link configured to facilitate an emergency contact connection upon actuation; iii) sending a signal to automatically facilitate an emergency contact connection; iv) initiating a patient health questionnaire protocol; v) generating a prompt for selecting a crisis management tool; vi) automatically initiating a crisis management tool; or vii) any combination of i-vi.

Example 3 is the system of example(s) 1 or 2, wherein the operations further include: presenting a crisis confirmation prompt in response to determining that the input phrase triggers the second classifier; and receiving a confirmation response in response to presenting the confirmation prompt, the confirmation response including a confirmation of the crisis situation or a denial of the crisis situation, wherein executing the abatement protocol occurs in response to receiving the confirmation of the crisis situation.

Example 4 is the system of example(s) 3, wherein the operations further include: identifying a trigger phrase in response to determining that the input phrase triggers the second classifier, wherein the trigger phrase includes a portion of the input phrase that matched a regular expression when the second classifier is the pattern matching classifier, and wherein the trigger phrase includes the input phrase when the second classifier is the trained machine learning classifier; and presenting a denial prompt in response to receiving the denial of the crisis situation, wherein presenting the denial prompt includes using the trigger phrase.

Example 5 is the system of example(s) 4, wherein the operations further include: logging the confirmation response in association with the trigger phrase; and updating at least one of the first classifier and the second classifier using the logged confirmation response and the trigger phrase.

Example 6 is the system of example(s) 4 or 5, wherein executing the abatement protocol includes scheduling a follow-up contact for a future time, wherein the operations further include presenting a follow-up message at the future time, and wherein presenting the follow-up message includes presenting the trigger phrase.

Example 7 is the system of example(s) 1-6, wherein the operations further include determining a crisis score using the input phrase, wherein generating the trigger signal is further based on a determination that the crisis score is outside of a threshold range.

Example 8 is the system of example(s) 1-7, wherein the operation further include: determining a crisis score using the input phrase; accessing one or more historical crisis scores; determining a crisis score trend using the crisis score and the one or more historical crisis scores; and determining a future crisis score using the crisis score and the crisis score trend, wherein generating the trigger signal is further based on a determination that the future crisis score is outside of a threshold range.

Example 9 is the system of example(s) 1-8, wherein the first classifier is the pattern matching classifier and the second classifier is the trained machine learning classifier.

Example 10 is the system of example(s) 1-9, wherein the trained machine learning classifier is trained using a set of training input phrases that were determined to not trigger the pattern matching classifier.

Example 11 is the system of example(s) 1-10, wherein the trained machine learning classifier is trained using a set of training input phrases including a first subset of training input phrases associated with crisis situations and a second subset of training input phrases not associated with crisis situations.

Example 12 is a computer-implemented method, comprising: receiving an input phrase associated with a crisis situation; applying a first classifier on the input phrase to determine that the input phrase does not trigger the first classifier; applying a second classifier on the input phrase to determine that the input phrase triggers the second classifier, wherein the first classifier is one of a pattern matching classifier and a trained machine learning classifier, and wherein the second classifier is the other of the pattern matching classifier and the trained machine learning classifier; generating a trigger signal in response to determining that the input phrase triggers the second classifier; and executing an abatement protocol in response to generation of the trigger signal, wherein execution of the abatement protocol is intended to mitigate the crisis situation.

Example 13 is the computer-implemented method of example(s) 12, wherein executing the abatement protocol includes i) accessing and presenting a text string containing emergency contact information, ii) accessing and presenting a link configured to facilitate an emergency contact connection upon actuation; iii) sending a signal to automatically facilitate an emergency contact connection; iv) initiating a patient health questionnaire protocol; v) generating a prompt for selecting a crisis management tool; vi) automatically initiating a crisis management tool; or vii) any combination of i-vi.

Example 14 is the computer-implemented method of example(s) 12 or 13, further comprising: presenting a crisis confirmation prompt in response to determining that the input phrase triggers the second classifier; and receiving a confirmation response in response to presenting the confirmation prompt, the confirmation response including a confirmation of the crisis situation or a denial of the crisis situation, wherein executing the abatement protocol occurs in response to receiving the confirmation of the crisis situation.

Example 15 is the computer-implemented method of example(s) 14, further comprising: identifying a trigger phrase in response to determining that the input phrase triggers the second classifier, wherein the trigger phrase includes a portion of the input phrase that matched a regular expression when the second classifier is the pattern matching classifier, and wherein the trigger phrase includes the input phrase when the second classifier is the trained machine learning classifier; and presenting a denial prompt in response to receiving the denial of the crisis situation, wherein presenting the denial prompt includes using the trigger phrase.

Example 16 is the computer-implemented method of example(s) 15, further comprising: logging the confirmation response in association with the trigger phrase; and updating at least one of the first classifier and the second classifier using the logged confirmation response and the trigger phrase.

Example 17 is the computer-implemented method of example(s) 15 or 16, wherein executing the abatement protocol includes scheduling a follow-up contact for a future time, wherein the method further comprises presenting a follow-up message at the future time, and wherein presenting the follow-up message includes presenting the trigger phrase.

Example 18 is the computer-implemented method of example(s) 12-17, further comprising determining a crisis score using the input phrase, wherein generating the trigger signal is further based on a determination that the crisis score is outside of a threshold range.

Example 19 is the computer-implemented method of example(s) 12-18, further comprising: determining a crisis score using the input phrase; accessing one or more historical crisis scores; determining a crisis score trend using the crisis score and the one or more historical crisis scores; and determining a future crisis score using the crisis score and the crisis score trend, wherein generating the trigger signal is further based on a determination that the future crisis score is outside of a threshold range.

Example 20 is the computer-implemented method of example(s) 12-19, wherein the first classifier is the pattern matching classifier and the second classifier is the trained machine learning classifier.

Example 21 is the computer-implemented method of example(s) 12-20, wherein the trained machine learning classifier is trained using a set of training input phrases that were determined to not trigger the pattern matching classifier.

Example 22 is the computer-implemented method of example(s) 12-21, wherein the trained machine learning classifier is trained using a set of training input phrases including a first subset of training input phrases associated with crisis situations and a second subset of training input phrases not associated with crisis situations.

Example 23 is a computer-program product tangibly embodied in a non-transitory machine-readable storage medium, including instructions configured to cause a data processing apparatus to perform operations including: receiving an input phrase associated with a crisis situation; applying a first classifier on the input phrase to determine that the input phrase does not trigger the first classifier; applying a second classifier on the input phrase to determine that the input phrase triggers the second classifier, wherein the first classifier is one of a pattern matching classifier and a trained machine learning classifier, and wherein the second classifier is the other of the pattern matching classifier and the trained machine learning classifier; generating a trigger signal in response to determining that the input phrase triggers the second classifier; and executing an abatement protocol in response to generation of the trigger signal, wherein execution of the abatement protocol is intended to mitigate the crisis situation.

Example 24 is the computer-program product of example(s) 23, wherein executing the abatement protocol includes i) accessing and presenting a text string containing emergency contact information, ii) accessing and presenting a link configured to facilitate an emergency contact connection upon actuation; iii) sending a signal to automatically facilitate an emergency contact connection; iv) initiating a patient health questionnaire protocol; v) generating a prompt for selecting a crisis management tool; vi) automatically initiating a crisis management tool; or vii) any combination of i-vi.

Example 25 is the computer-program product of example(s) 23 or 24, wherein the operations further include: presenting a crisis confirmation prompt in response to determining that the input phrase triggers the second classifier; and receiving a confirmation response in response to presenting the confirmation prompt, the confirmation response including a confirmation of the crisis situation or a denial of the crisis situation, wherein executing the abatement protocol occurs in response to receiving the confirmation of the crisis situation.

Example 26 is the computer-program product of example(s) 25, wherein the operations further include: identifying a trigger phrase in response to determining that the input phrase triggers the second classifier, wherein the trigger phrase includes a portion of the input phrase that matched a regular expression when the second classifier is the pattern matching classifier, and wherein the trigger phrase includes the input phrase when the second classifier is the trained machine learning classifier; and presenting a denial prompt in response to receiving the denial of the crisis situation, wherein presenting the denial prompt includes using the trigger phrase.

Example 27 is the computer-program product of example(s) 26, wherein the operations further include: logging the confirmation response in association with the trigger phrase; and updating at least one of the first classifier and the second classifier using the logged confirmation response and the trigger phrase.

Example 28 is the computer-program product of example(s) 26 or 27, wherein executing the abatement protocol includes scheduling a follow-up contact for a future time, wherein the operations further include presenting a follow-up message at the future time, and wherein presenting the follow-up message includes presenting the trigger phrase.

Example 29 is the computer-program product of example(s) 23-28, wherein the operations further include determining a crisis score using the input phrase, wherein generating the trigger signal is further based on a determination that the crisis score is outside of a threshold range.

Example 30 is the computer-program product of example(s) 23-29, wherein the operation further include: determining a crisis score using the input phrase; accessing one or more historical crisis scores; determining a crisis score trend using the crisis score and the one or more historical crisis scores; and determining a future crisis score using the crisis score and the crisis score trend, wherein generating the trigger signal is further based on a determination that the future crisis score is outside of a threshold range.

Example 31 is the computer-program product of example(s) 23-29, wherein the first classifier is the pattern matching classifier and the second classifier is the trained machine learning classifier.

Example 32 is the computer-program product of example(s) 23-31, wherein the trained machine learning classifier is trained using a set of training input phrases that were determined to not trigger the pattern matching classifier.

Example 33 is the computer-program product of example(s) 23-32, wherein the trained machine learning classifier is trained using a set of training input phrases including a first subset of training input phrases associated with crisis situations and a second subset of training input phrases not associated with crisis situations.

What is claimed is:

1. A method, comprising:
   obtaining training data comprising training input phrases, each training input phrase being associated with a label indicative of whether the respective training input phrase is associated with a crisis situation;
   training a machine learning classifier using the training input phrases and their respective labels;
   receiving an input phrase;
   applying the input phrase to a machine learning classifier to determine whether the input phrase triggers the machine learning classifier;
   determining a crisis score using the input phrase;
   accessing one or more historical crisis scores; and
   executing an abatement protocol in response to determining that the input phrase triggers the trained machine learning classifier, wherein execution of the abatement protocol is further based on the crisis score and the one or more historical crisis scores.

2. The method of claim 1, wherein the machine learning classifier is a transformer-based machine learning classifier initially trained using pre-training training data for a language prior to the training the machine learning classifier using the training input phrases.

3. The method of claim 1, further comprising:
   determining a crisis score trend using the crisis score and the one or more historical crisis scores; wherein execution of the abatement protocol is further based on the crisis score trend.

4. The method of claim 1, further comprising:
   obtaining additional training data, the additional training data including one or more additional input phrases previously supplied to the trained machine learning classifier, each of the one or more additional input phrases being associated with a respective label indicative of whether a user confirmed or denied a respective crisis situation after the respective additional input phrase triggered the trained machine learning classifier, and
   further training the trained machine learning classifier based at least in part on the additional training data, wherein further training occurs prior to receiving the input phrase.

5. The method of claim 4, wherein each of the additional input phrases was previously supplied to the trained machine learning classifier and triggered the trained machine learning classifier.

6. The method of claim 1, wherein executing the abatement protocol includes i) accessing and presenting a text string containing emergency contact information, ii) accessing and presenting a link configured to begin initiation of an emergency contact connection upon actuation; iii) sending a signal to automatically begin initiation of an emergency contact connection; iv) initiating a patient health questionnaire protocol; v) generating a prompt for selecting a crisis management tool; vi) automatically initiating a crisis management tool; or vii) any combination of i-vi.

7. The method of claim 1, wherein receiving the input phrase occurs via a text-based communication protocol, wherein executing the abatement protocol includes automatically initiating a crisis management tool via the text-based communication protocol, the crisis management tool including a workflow of prompts and/or comments for mitigating the crisis situation.

8. The method of claim 7, wherein the crisis management tool, when initiated, facilitates:
   providing, via the text-based communication protocol, a series of questions from a patient health questionnaire; and
   receiving, via the text-based communication protocol, a response for each question of the series of questions.

9. A system, comprising:
   one or more data processors; and
   a non-transitory computer-readable storage medium containing instructions which, when executed on the one or more data processors, cause the one or more data processors to perform operations including:
      obtaining training data comprising training input phrases, each training input phrase being associated with a label indicative of whether the respective training input phrase is associated with a crisis situation;
      training a machine learning classifier using the training input phrases and their respective labels;
      receiving an input phrase;
      applying the input phrase to a machine learning classifier to determine whether the input phrase triggers the machine learning classifier;
      determining a crisis score using the input phrase;
      accessing one or more historical crisis scores; and
      executing an abatement protocol in response to determining that the input phrase triggers the trained machine learning classifier, wherein execution of the abatement protocol is further based on the crisis score and the one or more historical crisis scores.

10. The system of claim 9, wherein the machine learning classifier is a transformer-based machine learning classifier initially trained using pre-training training data for a language prior to the training the machine learning classifier using the training input phrases.

11. The system of claim 9, wherein the operations further include:
   determining a crisis score trend using the crisis score and the one or more historical crisis scores; wherein execution of the abatement protocol is further based on the crisis score trend.

12. The system of claim 9, wherein the operations further include:
   obtaining additional training data, the additional training data including one or more additional input phrases previously supplied to the trained machine learning classifier, each of the one or more additional input phrases being associated with a respective label indicative of whether a user confirmed or denied a respective crisis situation after the respective additional input phrase triggered the trained machine learning classifier, and
   further training the trained machine learning classifier based at least in part on the additional training data, wherein further training occurs prior to receiving the input phrase.

13. The system of claim 12, wherein each of the additional input phrases was previously supplied to the trained machine learning classifier and triggered the trained machine learning classifier.

14. The system of claim 9, wherein executing the abatement protocol includes i) accessing and presenting a text string containing emergency contact information, ii) accessing and presenting a link configured to begin initiation of an emergency contact connection upon actuation; iii) sending a signal to automatically begin initiation of an emergency contact connection; iv) initiating a patient health questionnaire protocol; v) generating a prompt for selecting a crisis management tool; vi) automatically initiating a crisis management tool; or vii) any combination of i-vi.

15. The system of claim 9, wherein receiving the input phrase occurs via a text-based communication protocol, wherein executing the abatement protocol includes automatically initiating a crisis management tool via the text-based communication protocol, the crisis management tool including a workflow of prompts and/or comments for mitigating the crisis situation.

16. The system of claim 15, wherein the crisis management tool, when initiated, facilitates:
   providing, via the text-based communication protocol, a series of questions from a patient health questionnaire; and
   receiving, via the text-based communication protocol, a response for each question of the series of questions.

17. A computer-program product tangibly embodied in a non-transitory machine-readable storage medium, including instructions configured to cause a data processing apparatus to perform operations including:
   obtaining training data comprising training input phrases, each training input phrase being associated with a label indicative of whether the respective training input phrase is associated with a crisis situation;
   training a machine learning classifier using of the training input phrases and their respective labels;
   receiving an input phrase;
   applying the input phrase to a machine learning classifier to determine whether the input phrase triggers the machine learning classifier;
   determining a crisis score using the input phrase;
   accessing one or more historical crisis scores; and
   executing an abatement protocol in response to determining that the input phrase triggers the trained machine learning classifier, wherein execution of the abatement protocol is further based on the crisis score and the one or more historical crisis scores.

18. The computer-program product of claim 17, wherein the machine learning classifier is a transformer-based machine learning classifier initially trained using pre-training training data for a language prior to the training the machine learning classifier using the training input phrases.

19. The computer-program product of claim 17, wherein the operations further include:

determining a crisis score trend using the crisis score and the one or more historical crisis scores; wherein execution of the abatement protocol is further based on the crisis score trend.

20. The computer-program product of claim 17, wherein the operations further include:
   obtaining additional training data, the additional training data including one or more additional input phrases previously supplied to the trained machine learning classifier, each of the one or more additional input phrases being associated with a respective label indicative of whether a user confirmed or denied a respective crisis situation after the respective additional input phrase triggered the trained machine learning classifier, and
   further training the trained machine learning classifier based at least in part on the additional training data, wherein further training occurs prior to receiving the input phrase.

21. The computer-program product of claim 20, wherein each of the additional input phrases was previously supplied to the trained machine learning classifier and triggered the trained machine learning classifier.

22. The computer-program product of claim 17, wherein executing the abatement protocol includes i) accessing and presenting a text string containing emergency contact information, ii) accessing and presenting a link configured to begin initiation of an emergency contact connection upon actuation; iii) sending a signal to automatically begin initiation of an emergency contact connection; iv) initiating a patient health questionnaire protocol; v) generating a prompt for selecting a crisis management tool; vi) automatically initiating a crisis management tool; or vii) any combination of i-vi.

23. The computer-program product of claim 17, wherein receiving the input phrase occurs via a text-based communication protocol, wherein executing the abatement protocol includes automatically initiating a crisis management tool via the text-based communication protocol, the crisis management tool including a workflow of prompts and/or comments for mitigating the crisis situation.

24. The computer-program product of claim 23, wherein the crisis management tool, when initiated, facilitates:
   providing, via the text-based communication protocol, a series of questions from a patient health questionnaire; and
   receiving, via the text-based communication protocol, a response for each question of the series of questions.

* * * * *